(12) United States Patent
Kiessling et al.

(10) Patent No.: US 10,894,094 B2
(45) Date of Patent: Jan. 19, 2021

(54) TETRAPYRROLES CONJUGATES AS MRI CONTRAST AGENT

(71) Applicant: NANO4IMAGING GMBH, Düsseldorf (DE)

(72) Inventors: Fabian Kiessling, Aachen (DE); Paul Borm, Meerssen (NL); Jozef Cremers, Heerlen (NL); Nihan Güvener, Aachen (DE)

(73) Assignee: NANO4IMAGING GMBH, Düsseldorf (DE)

( * ) Notice: Subject to any disclaimer, the term of this patent is extended or adjusted under 35 U.S.C. 154(b) by 0 days.

(21) Appl. No.: 16/333,343

(22) PCT Filed: Aug. 31, 2017

(86) PCT No.: PCT/EP2017/071931
§ 371 (c)(1),
(2) Date: Mar. 14, 2019

(87) PCT Pub. No.: WO2018/050450
PCT Pub. Date: Mar. 22, 2018

(65) Prior Publication Data
US 2019/0209714 A1    Jul. 11, 2019

(30) Foreign Application Priority Data
Sep. 15, 2016    (EP) .................................... 16189057

(51) Int. Cl.
*A61K 49/08*    (2006.01)
*A61K 49/10*    (2006.01)
*A61K 49/14*    (2006.01)
*C07D 487/22*    (2006.01)

(52) U.S. Cl.
CPC .......... *A61K 49/106* (2013.01); *A61K 49/085* (2013.01); *A61K 49/146* (2013.01); *C07D 487/22* (2013.01)

(58) Field of Classification Search
CPC ... A61K 49/106; A61K 51/088; C07D 403/14
See application file for complete search history.

(56) References Cited

U.S. PATENT DOCUMENTS

| 5,008,388 A | 4/1991 | Ingberg et al. |
| 2002/0183470 A1 | 12/2002 | Tripathy et al. |
| 2006/0013774 A1 | 1/2006 | Port |

FOREIGN PATENT DOCUMENTS

| DE | 10006570 A1 | 8/2001 |
| EP | 0470086 B1 | 1/1995 |
| EP | 1148057 A1 | 10/2001 |
| RU | 2238950 C2 | 10/2004 |
| WO | 2008135139 A1 | 11/2008 |
| WO | WO 2008/135139 | * 11/2008 |
| WO | 2014144633 A1 | 9/2014 |
| WO | 2015076312 A1 | 5/2015 |

OTHER PUBLICATIONS

Simakova et al., Angewandte Communications, Polymerization, Bioinspired Iron-Based Catalyst for Atom Transfer Radical Polymerization, International Edition, 2013, vol. 52, No. 46, p. 12148-12151.
Nagarajan et al., A stable biomimetic redox catalyst obtained by the enzyme catalyzed amidation of iron porphyrin, Green Chemistry, 2009, vol. 11, No. 3, p. 334-338.
Sondhi et al., Synthesis of hemin and porphyrin derivatives and their evaluation for anticancer activity, Indian Journal of Chemistry, Section B: Organic Chemistry Including Medicinal Chemistry, 2001, vol. 40B, No. 2, p. 113-119.
Spaltro et al., Synthesis and Characterization of Conjugates of Poly (a-Amino Acids) and Manganese (III) Protoporphyrin IX as Relaxation Enhancement Agents for MRI*, Journal of Applied Polymer Science, 1990, vol. 41, No. 5-6, p. 1235-1249.
Office Action issued by Japanese Patent Office dated May 15, 2020, in connection with JP 2019-515541.
International Preliminary Report on Patentability for PCT/EP2017/071931 dated Mar. 19, 2019.
International Search Report and Written Opinion of the International Searching Authority for International Application No. PCT/EP2017/071931 dated Nov. 22, 2017.
Monzani, E., et al., "Properties and Reactivity of Myoglobin Reconstituted with Chemically Modified Protohemin Complexes", Biochemistry, vol. 39, No. 31, pp. 9571-9582 (2000).
Roncone, R., et al., "Catalytic activity, stability, unfolding, and degradation pathways of engineered and reconstituted myoglobins", Journal of Biological Inorganic Chemistry, vol. 10, No. 1, pp. 11-24 (2005).
Spaltro, S.M., et al., "Synthesis and Characterization of Conjugates of Poly (&-Amino Acids) and Manganese (III) Protoporphyrin IX as Relaxation Enhancement Agents for MRI," Journal of Applied Polymer Science, pp. 1235-1249 (1990).

* cited by examiner

*Primary Examiner* — Michael G. Hartley
*Assistant Examiner* — Jagadishwar R Samala
(74) *Attorney, Agent, or Firm* — Heslin Rothenberg Farley & Mesiti P.C.

(57) ABSTRACT

The invention relates to the use of tetrapyrroles conjugated compounds as contrast agent in magnetic resonance imaging (MRI). In particular conjugates of natural hemin that can be embedded in gels and implants to image local delivery in MRI.

5 Claims, 3 Drawing Sheets

TETRAPYRROLES CONJUGATES AS MRI CONTRAST AGENT

CROSS REFERENCE TO RELATED APPLICATIONS

This application is a national stage filing under section 371 of International Application No. PCT/EP2017/071931, filed Aug. 31, 2017, and published in English on Mar. 22, 2018, as WO 2018/050450 A1, and claims priority of European Patent Application No. 16189057.9, filed on Sept. 15, 2016, the entire disclosures of the foregoing applications being hereby incorporated herein by reference.

The invention is related to tetrapyrroles conjugated compounds a method for producing and the use of such conjugates, which comprise within one molecule at least one tetrapyrroles compound, at least one at least partially water-soluble compound and their salts, solvates and solvates of these salts.

The global market for contrast media, which are substances used in medical imaging which enhance the visibility of structures or fluids within the body, is set to rise from just over $4.3 billion in 2015 to over $6 billion by 2022, representing a compound annual growth rate of 4.9%, according to consulting firm GlobalData. It has to be stated that this growth, which will occur across the 10 major markets (10 MM) of the US, France, Germany, Italy, Spain, the UK, Japan, Brazil, China, and India, will be driven by a number of factors, including increases in the number of annual computed tomography (CT), magnetic resonance imaging (MRI), and echocardiogram procedures as well as an increasing disease burden across the 10 MM.

More than 20,000,000 magnetic resonance imaging (MRI) procedures are performed annually worldwide for various clinical indications. In the light of the growing importance of the use of ionizing radiation in therapy and of the growing interest in minimally invasive therapies, it is unsurprising that magnetic resonance tomography has been slowly establishing itself in the area of radiology since about 1995. While magnetic resonance tomography was originally developed for diagnostic images, it is now used as a tool for performing and assessing minimally invasive therapeutic interventions. The relatively new field of use concerns areas such as intraoperative and endovascular MRI procedures. Minimally invasive endovascular procedures play an increasingly important role in the treatment of patients. For many reasons, the radiological procedures are attractive alternatives to surgical interventions and corresponding treatments. In that view contrast agents play an important role in daily medical procedures as they help to construct MRI images. Currently used contrast agents are the low molecular weight gadolinium complexes such as Magnavist® mainly by reducing T1 or colloidal iron complexes such as Combidex® by decreasing T2 or T2*.(susceptibility).

On its own, gadolinium can be toxic. When used in contrast agents, gadolinium binds with a molecule called a chelating agent, which controls the distribution of gadolinium within the body. Safety concerns about gadolinium erupted in 2006, when the use of GBCAs was linked to the development of nephrogenic systemic fibrosis (NSF), a sometimes fatal condition. Recent studies have raised new concerns about gadolinium's safety, particularly regarding whether residual traces of the element remain in the brains of individuals who received contrast. In a recent hospital based case-control study, Kanda and colleagues started with a pool of 190 subjects for whom autopsy was performed between 2010 and 2013 at the facility. The pool of subject was broken down into several groups; one group contained 5 randomly selected patients who were given gadolinium contrast more than twice (the GBCA group). These subjects received gadopentetate dimeglumine (Magnevist®, Bracco Imaging), gadodiamide (Omniscan®, GE Healthcare); or gadoteridol (ProHance®, Bracco). They received a dose of 0.1 mmol/kg of body weight for each examination. The study also included five people as a control group who had never received any contrast material (non-GBCA group).

None of the subjects in either group had a history of severe renal dysfunction or acute renal failure. The researchers used inductively coupled plasma mass spectroscopy (ICP-MS) to evaluate the accumulation of gadolinium in brain tissues, including the dentate nucleus and globus pallidus. Both the dentate nucleus and globus pallidus control the body's voluntary movements. Upon analysis, the researchers found traces of gadolinium in specimens from all five people in the GBCA group (mean, 0.25 µg/g of brain tissue), with significantly higher concentrations in each region, compared with those who never had gadolinium contrast. In addition, in the GBCA group, the dentate nucleus and globus pallidus showed significantly higher gadolinium concentrations than other regions of the brain. Most notably, the presence of gadolinium accumulation was discovered in subjects with no history of severe renal dysfunction. These findings will add to the discussion on the safety of Gadolinium derived T1 contrast agents. $T_2$ contrast agents are also gradually disappearing from the market. Therefore there is a large need for new, non-toxic contrast agents that can be used in $T_1$, $T_2$ or both types of imaging.

Hence it was the aim of investigations to achieve a non-toxic MRI contrast agent, whereby the imaging results are comparable to those with Gd-contrast agents.

Hemin is a natural, $Fe^{3+}$-containing red blood pigment, which is commercially available from various companies as a pure substance. It is particularly suitable for MRI measurements by the configuration of 3d orbital electrons. The iron $Fe^{3+}$ion in hemin is in a high-spin state which means that unpaired electron orbitals are present, which means that both spin-spin interactions are more likely to occur. Using a weak ligand such chlorine, isothiocyanates and imidazole-rings are known to shift the high-spin state. For example a nitroimidazole-supporting porphyrin complex has been claimed for missile therapy in which MRI visibility and radiotherapy can be combined (EP 114 8057). Other patents have incorporated other metal ions such as manganese (Mn) in natural and new porphyrins to show that certain chelates have a high relaxivity beyond 1.5 Tesla (US 20 060 137 74), and can be used diagnostic and therapeutic purposes.

However Hemin is practically insoluble in physiological conditions and would immediately intercepted by the application of the liver. Only through protein binding hemin conjugates can be made which may be useful as MR contrast agents. In this subject the EP 0470 086 B1 describes the synthesis of a water-soluble compound with basic amino-acids, for example L-arginine. The resulting compound is claimed for treatment of various types of anemia and porphyrism. Hemin-protein conjugates have been claimed for use in MRI as contrast agent, but particularly using proteins such as albumin to prevent recognition by the immune system as foreign protein (DE 100 06 570), and facilitating intracellular accumulation to allow tumor and inflammatory site imaging.

Further state of the art like Suree M Spaltro et al. "synthesis and characterization of conjugates of poly (amino acids) and manganese (III) IX as relaxation enhancement agents for mri" in Journal of applied polymer science, 1 Jan. 1990 discloses adducts of Mn-containing porphyrin with polylysine or polyglutamatic acid, wherein the reaction is carried out in a mixture of DMF and water.

Another disclosure like Raffaella Roncone et al. "catalytic activity, stability, unfolding an degradation pathways of properties and reactivity of myoglobin reconstituted with chemically modified protohemin complexes" in Biochemistry, vol. 39, no. 31, 1 Aug. 2000, pages 11-24, describes the reaction of protohemin chloride with histamine methyl ester in DMF.

Enrico Monzani et al. "Properties and reactivity of myoglobin reconstituted with chemically modified protohemin complexes", Biochemistry, vol. 39, no. 31, 1 Aug. 2000, pages 9571-9582

RU 2238950 C2 discloses the reaction of protohemin chloride with Fmoc-Arg (Pmc)-ala-O-tBu in DMF.

In WO 2014/144633 A1 are disclosed derivates of hemin wherein substituents can be amino acids, peptides or derivates thereof and the central ion can be Fe and one of its ligands is chloride.

The drawback of such patents is that most of them are using nanoparticles which in some cases could get in the blood stream and have significant toxicological concern. Based on the above mentioned examples that disclose the use of hemin derivatives as injectable MRI contrast agents for specific biomedical and as well as in order to overcome all issues related to nanoparticles, the object of the present invention is to make hemin or hemin derivatives available as contrast agents to permit high-quality visualization in MR. In the context of the present invention, the MRI contrast agents are based on Hem in as an iron-containing tetrapyrrole. More specifically, it is protoporphyrin IX containing a ferric iron ion (heme b) with a chlorid ligand and is a degradation product of the oxygen carrying hemoglobin.

The problem to be solved by the invention is hence to find hemin like tetrapyrrole conjugates as a non-toxic contrast agent with good imaging results, which can be used to image implants, carrier gels and even as contrast agents.

Figure 1:
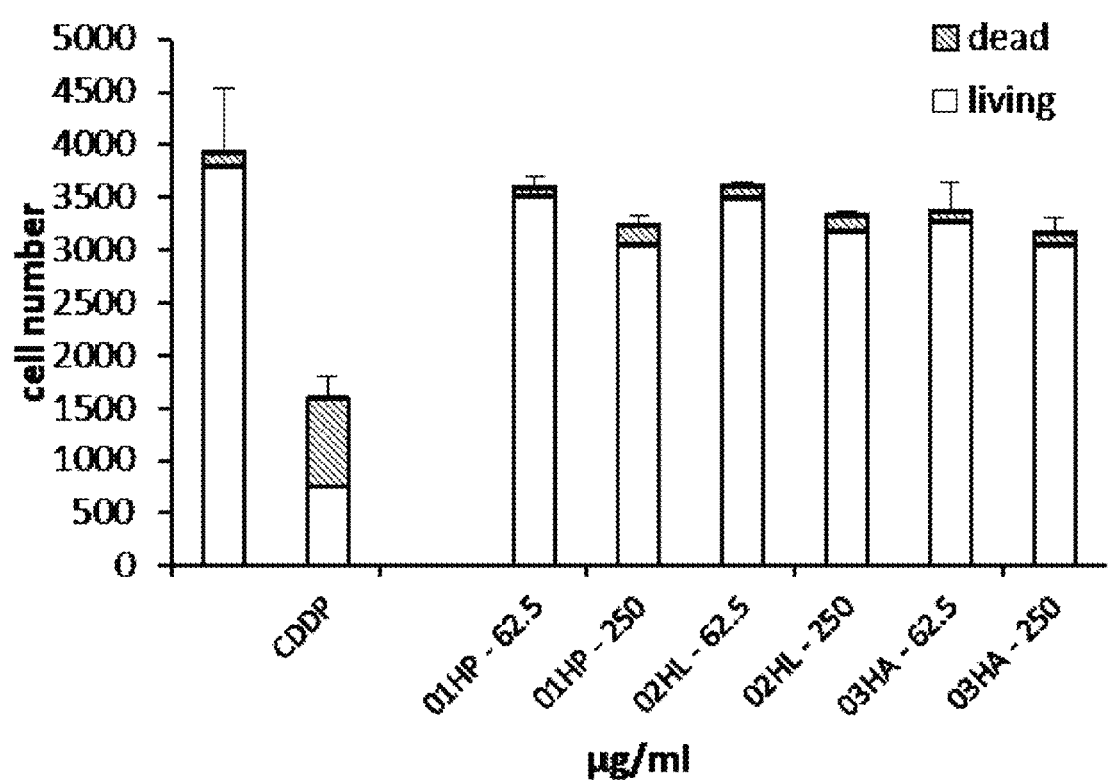
FIG. 1 shows the total cell number of HCT 116 cells (dead/alive) after 24 hours incubation with different concentrations of hemin derivatives is shown, in accordance with aspects of the present disclosure.

The solution of the problem is given by the formulation of the independent claims 1 and 5.

In the context of the present invention, a condition is preferred in which the Fe II/Fe III tetrapyrrole conjugates contrast agents are biocompatible. In particular, compounds are preferred which are characterized in that the Fe II/Fe III tetrapyrroles contrast agents are porphyrins A particular embodiment of the present invention is characterized in that the cofactors are derivatives of heme proteins (i.e heme a, heme b, heme c and heme o).

A particular embodiment of the present invention is characterized in that, the Fe II/Fe III tetrapyrrole contrast agents is conjugated with water soluble polymers or treated with basic amino acids such as ARG, LYS.

A particular embodiment of the present invention is characterized in that the Fe II/Fe III tetrapyrroles or porphyrin conjugate contrast agents is functionalized or covalently bound to for example, polyacrylates, Collagen, Hydrogels, polyvinyl lactams, PEG, PGLA, polyacrylic acid, PVP, multivalent polymers and copolymers and mixtures of these components.

A particular embodiment of the present invention is characterized in that, the Fe II/Fe III tetrapyrroles or porphyrin conjugate contrast agents contain a spacer between the tetrapyrroles or porphyrin ring and a polymer chain.

A particular embodiment of the present invention is characterized in that multiple Fe II/Fe III tetrapyrroles or porphyrin conjugate contrast agents can be attached to the polymeric chain.

A particular embodiment of the present invention is characterized in that, the Fe II/Fe III tetrapyrroles or porphyrin conjugate contrast agents is dissolved in polar carrier liquids or hydrogels, that are able to exchange hydrogen atoms.

Preferred Fe II/Fe III tetrapyrroles or porphyrin conjugate contrast agents according to the present invention, which are characterized in that, the Fe II/Fe III tetrapyrroles or porphyrin conjugate contrast agents are partially solubilized and suspended in a carrier liquid.

EXAMPLES

Example 1

An example of a PEGylation reaction of a tetrapyrroles compound like hemin is described in the following instruction. Hemin (29 mg, 0.0445 mmol ) is dissolved in Tetrahydrofuran THF (10 mL) and triethylamine (0.6 mL) is added. Subsequently, the suspension is cooled to 0° C. and allowed to stir for 1 hour. Next, ethylchloroformate (0.425 mL, 4.46 mmol) is added and stirring was continued at 0° C. for another 2 hours. The mixture was filtered and the filtrate was treated with ethylenediamine (0.3 mL 4.48 mmol) and stirred at room temperature overnight. The mixture was concentrated in vacuo and used as such in the next reaction (I).

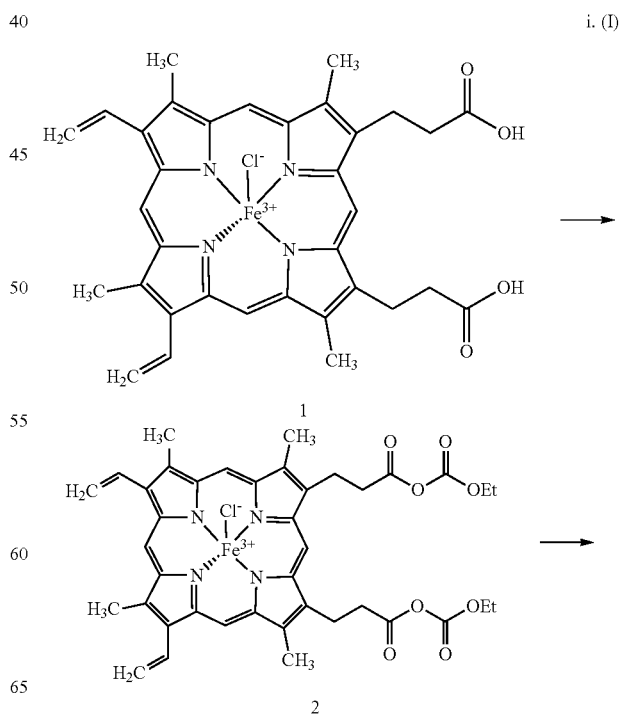

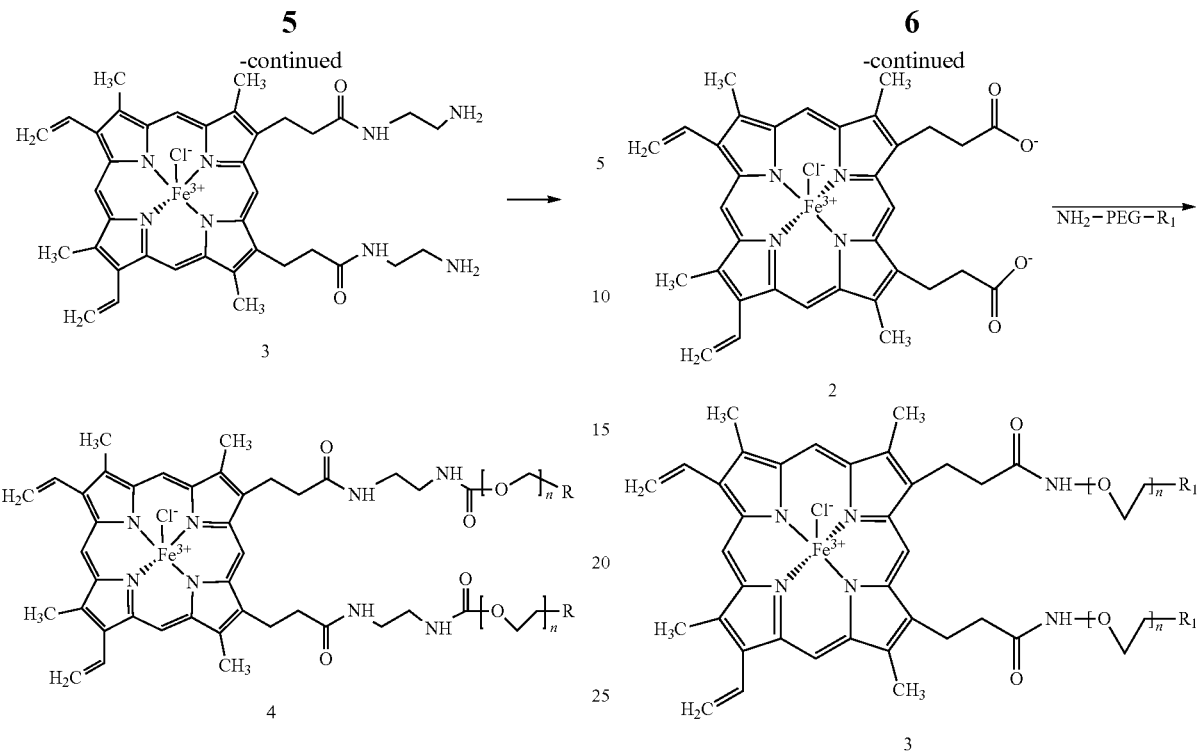

Hemin derivative (3) was yielded with an amount of (15 mg, 50%). The hemin derivative was dissolved in chloroform and treated with succinymidyl PEG with different molecular weights gave after dialysis the desired PEGylated hemin derivative (4).

Example 2

An example of a further PEGylation reaction is described in (II) below. 0.15 ml Triethylamine is added to a suspension of 32.6 g Hemin (1) in 100 ml Tetrahydrofurane (THF) and suspension cooled down to 0° C. for 1 hour. Then 19.2 mg of 1-ethyl-3-(3-dimethylaminopropyl)carbodiimide (EDC) is added to a suspension of Hemin to activate the carboxyl groups (2) within.

i.

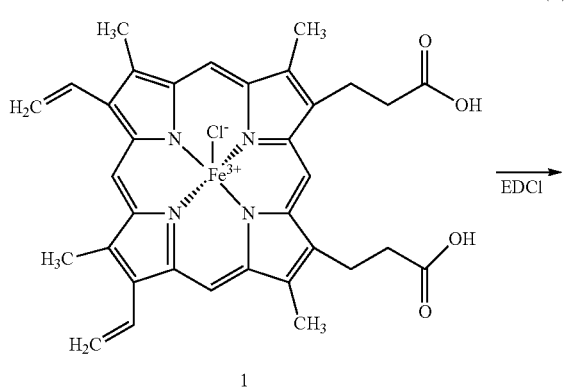

(II)

An amine-PEG compound is added directly after the reaction to be further proceed at room temperature overnight with stirring. Treatment with amine-PEG with different molecular weights gave after dialysis the desired pegylated hemin derivative (3).

Example 3

An example of the process to solubilize hemin by treating it with amino acids as base is described below, similar to procedure as described by Ingberg et al. in U.S. Pat. No. 5,008,388 A. 6.52 g of crystalline hemin (0.01 M) and 3.48 g of crystalline L-arginine (0.02 M) were vigorously stirred for 10 to 15 hours in a beaker provided with a mechanical stirrer and containing a solvent mixture of 300 ml. of acetone and 20 ml. of water. The product formed was filtered off, washed with acetone, and dried. Yield of hemin arginate: 9.5 g. (95%). Insoluble residue, determined by the method mentioned above: 0.14 g. (1.4%).

Example 4

An example of the process to solubilize hemin by treating it with amino acids as base is described below, similar to procedure as described by Ingberg et al. in U.S. Pat. No. 5,008,388 A. 6.52 g. of crystalline hemin (0.01 M) and 4.39 g. of 30 crystalline L-lysine (0.03 M) were treated as described in Example 2. Yield of hemin lysinate: 10.8 g. (99%). Insoluble residue: 0.020 g. (0.20%). It appears that the optimal molar proportion of hemin 35 to arginate is 1:3, because this gave the highest yield of hemin arginate, while the amount of insoluble residue was minimal.

Example 5

An example of incorporation of hemin derivatives in a hydrogel is detailed below:

Hyaluronic acid based hydrogels (1 g) was dissolved in PBS buffer (20 mL) and cooled to 0° C. Subsequently, EDC (2.5 g, 16.5 mmol) and NHS (0.345 g, 3.0 mmol) were added and allowed to stir for 15 minutes. Aminated hemin 2 (9.7 g, 15 mmol) was added and the reaction was continued for 24 h at room temperature. After dialysis (MCOW 2 k), the product was obtained and confirmed with UV-VIS.

Example 6

The derivatives of hemin complex structure with/without gel matrix as described vide supra are being used as CEST or chemical exchange saturation transfer agent for MR imaging. The complex hemin derivative with Hyaluronic acid gel within different coupling ratios have resulted in a novel MRI in vitro contrast and formulations are being applied to different cell lines for being imaged via MRI for detecting the presence of contrast agent presenting cell viability in the subject at the site, thereby visualizing contrast agent presenting cell activation in the subject e.g. fibroblasts, smooth muscle cells etc.

Toxicity Studies (In Vitro)

The toxicity of hemin water soluble derivatives (arginate-HA, lysinate-HL) and the PEGylated hemine (HP) was tested in HCT 116 cell line in concentrations up to 250 ug/ml up to 24 hours incubation. This concentration was chosen since it would be equivalent to the maximal plasma concentration after injection of 1 mmol/kg in a patient the common dose of cyclic Gd-contrast such as Omniscan.

In FIG. 1 the total cell number of HCT 116 cells (dead/alive) after 24 hours incubation with different concentrations of hemin derivatives is shown. Cisplatin (CDDP) was used as a positive control in a concentration of 50 μmol/L.

Figure 2:
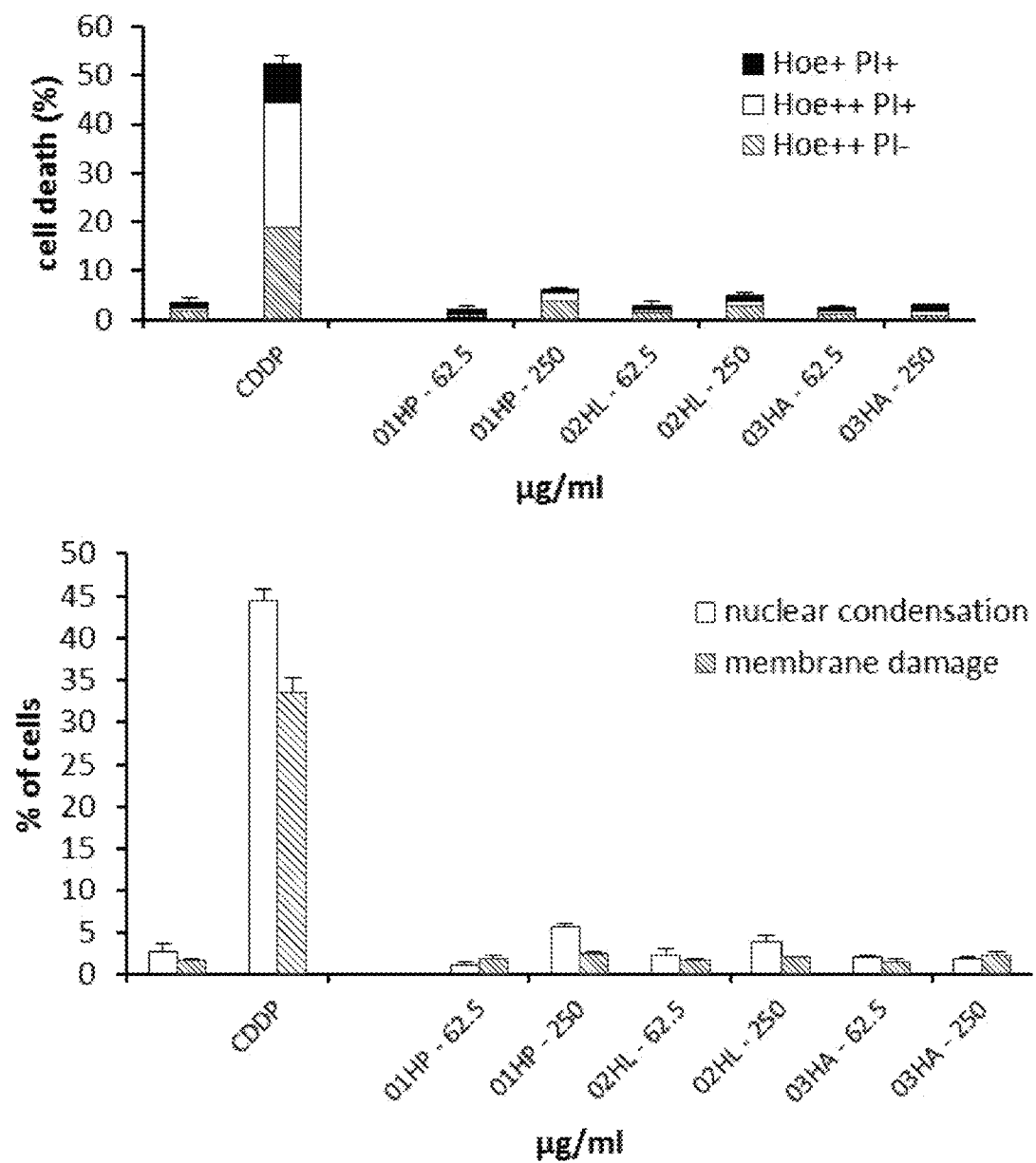
FIG. 2 shows the amount of early apoptopic cells upon incubation of HCT 116 cells for 24 hours incubation with different concentrations of hemin derivatives (upper panel) and the amount of cells with nuclear condensation and with membrane damage (lower panel), in accordance with aspects of the present disclosure.

In FIG. 2 the upper panel shows the amount of early apoptotic cells upon incubation of HCT 116 cells for 24 hours incubation with different concentrations of hemin derivatives is shown. CDDP was used a positive control in a concentration of 50 μmol/L. The lower panel shows the amount of cells with nuclear condensation (significant apoptosis) and with membrane damage.

Scaffold Imaging

A set, 0.5% (w/v) collagen in 0.25M Acetic acid solution have been selected due to easy handling. Hemin Lysinate (HL) solutions in 1.5 ml PBS buffer were mixed with 1.5 ml collagen solution with final concentration of 0.1 mM to 1 mM HL and mixed at room temperature overnight. Two different phases occurred in the final composition so that homogeneity of the samples was not sufficient. The study discontinued.

In a second set of experiments, 0.5% (w/v) collagen tubular scaffolds without coil support were selected. Tubular shape was achieved after freeze-drying procedure. Tubular collagen scaffolds of 1.5 cm have introduced to HL solutions in 1.5 ml PBS buffer with final concentration of 0.1 mM to 1 mM HL and mixed at room temperature. Scaffold started to shrink and loose 3D structure immediately after introduction of HL. The study discontinued.

For the third study set, 0.5% (w/v) collagen tubular scaffolds with coil support were selected. The crosslinking procedure was complete and the end structures were stable in PBS buffer and pre-wetted for 30 mins before use. Tubular collagen scaffolds of 1.5 cm have introduced to HL solutions in 1.5 ml PBS buffer with final concentration of 0.1 mM to 1 mM HL and mixed at room temperature overnight. Supernatant solutions have collected from each sample to determine nonintegrated concentration of HL and labeled as HL-Day0 solutions. Following washing procedure with 1.5 ml PBS was performed in PBS solutions for the next 12 h and 24 h. Washing solutions have collected from each sample and labeled as HL-Day1 and HL-Day2.

For the fourth study set, the procedure described for the third set has followed with Hemin Arginate (HA) and 0.5% (w/v) collagen tubular scaffolds with coil. Cross-linked tubular collagen scaffolds of 1.5 cm have introduced to HA solutions in 1.5 ml PBS buffer with final concentration of 0.1 mM to 1 mM HA and mixed at room temperature overnight. Supernatant solutions have collected from each sample to determine nonintegrated concentration of HA and labeled as HA-Day0 solutions. Following washing procedure with 1.5 ml PBS was performed in PBS solutions for the next 12 h and 24 h. Washing solutions have collected from each sample and labeled as HA-Day1 and HA-Day2.

For the fifth study set, the procedure described for the third set has followed with Hemin-PEGs (HPEG) and 0.7% (w/v) collagen tubular scaffolds with coil due to sample availability. The HPEG samples were varied with different PEG lengths of 1 KDa, 5 KDa and 10 KDa. Cross-linked tubular collagen scaffolds in 1.5 ml PBS buffer have introduced to the three HPEG solutions in 1.5 ml PBS buffer with the maximum available concentration of each HPEG stock solutions and mixed at room temperature overnight. Supernatant solutions have collected from each sample to determine nonintegrated concentration of HPEG and labeled as HPEG-Day0 solutions. Following washing procedure with 1.5 ml PBS was performed in PBS solutions for the next 12 h and 24 h. Washing solutions have collected from each sample and labeled as HPEG-Day1 and HPEG-Day2.

Chemical Interaction: For the sixth study set, Hemin Lysinate (HL) was selected, the activation of carboxyl groups of HL was performed via EDC/NHS coupling in MES solution (Table 1) and dissolved each in 3 ml EDC/NHS solution* with content of 3.3 mM EDC. (*Ratio EDC:NHS was taken from a previous study with %5 (w/v) collagen tubular scaffolds as 0.5:2 which translated into weights as 15.625 mg EDC to 17.25 mg NHS for 25 ml MES buffer.)

TABLE 1

EDC/NHS coupling of Hemin Lysinate (HL) within a concentration range

| Sample Name | Content | Amount of HL (g) | Sample Volume (ml) |
|---|---|---|---|
| C × L 0.1 | 1 mg/ml | 0.003 | 3 |
| C × L 0.2 | 2 mg/ml | 0.006 | 3 |
| C × L 0.25 | 2.5 mg/ml | 0.0075 | 3 |
| C × L 0.5 | 5 mg/ml | 0.015 | 3 |

In meantime, 0.5% (w/v) non-crosslinked tubular collagen scaffolds with coils incubated in MES buffer for 30 mins for the transition to wet state and MES buffer has removed before application. After the activation of carboxyl groups of HL, samples have introduced collagen scaffolds and mixed under rolling for 4 h to achieve homogenous labeling.

The final samples were in dark-brown color and homogeneous (except the sample 0.25%). A small amount of samples have collected for histology. The samples then fixed to %1 agarose for MR measurement. Samples were further investigated with 3T Clinical MRI (Philips) and 11.7T preclinical MRI (Bruker). Images are given in FIG. 1 and relaxation times of each sample are given in Table 2. In each scan two regions of interest (ROI) have been selected and mean values of multiple slices are listed. ROIs were chosen as one on scaffold region and one on agarose as control which scaffolds were embedded in.

TABLE 2

Relaxation Times of Collagen Scaffolds with/-out Hemin lysinate at 11.7T MR

| Sample Name | $T_1$ (ms) | $T_2$ (ms) | T2* (ms) | Conc (mM) |
|---|---|---|---|---|
| C × L 0.1 | 1823 ± 36 | 187 ± 2 | 30.7 ± 0.5 | 1.3 |
| Control (agarose) | 2233 ± 33 | 116 ± 0.7 | — | — |
| C × L 0.20 | 2003 ± 28 | 190 ± 3 | 22.2 ± 0.8 | 2.6 |
| Control (agarose) | 2519 ± 25 | 108 ± 0.4 | — | — |
| C × L 0.5 | 1908 ± 29 | 194 ± 3 | 20.9 ± 0.8 | 6.5 |

MRI Conditions

Figure 3:
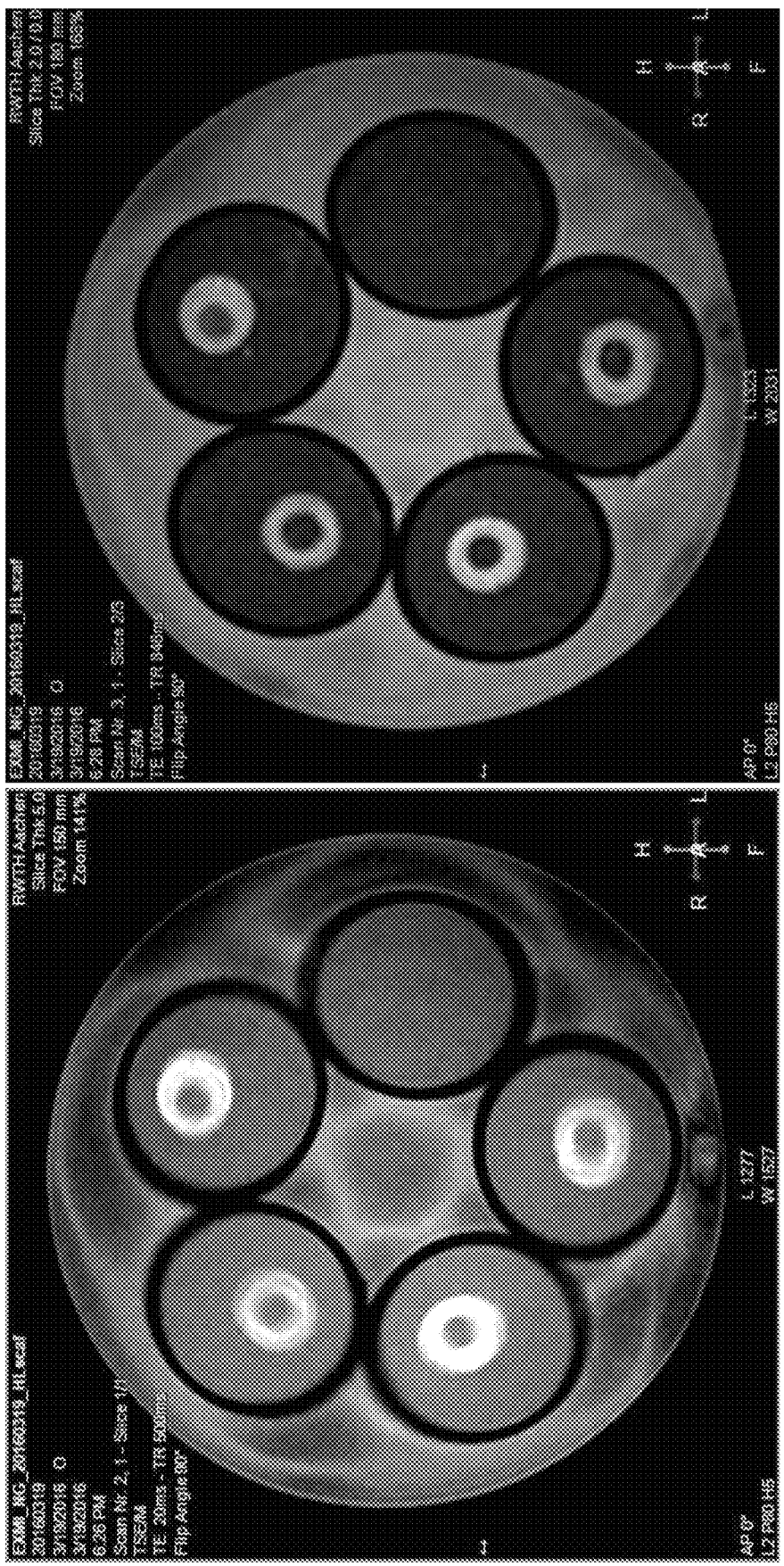
FIG. 3 shows MR Images of Collagen Scaffolds in accordance with aspects of the present disclosure.

Magnetic Resonance Imaging: Nuclear MR relaxometry of labeled scaffolds was performed in a clinical 3T whole-body MR scanner (Philips Achieva, Best, The Netherlands) using a knee coil (SENSE-flex-M; Philips, Best, The Netherlands) at room temperature. Longitudinal (T1) relaxation times were measured in 2D scan mode of turbo field echo sequences with a 10° flip angle refocusing pulses [TR=52 ms, TE=3-48 ms, number of echoes=10]. Transverse (T2) relaxation times were measured in 2D scan mode using a multi-slice, multi-shot spin-echo sequences with a 90° excitation pulse followed by a train of equally spaced 180° refocusing pulses [TR=1500 ms, TE=8-168 ms, number of echoes=20]. For T2* relaxometry, images at 32 echo times (TE range=3-99 ms) were acquired by using a multi-shot, multi-slice fast-field gradient-echo sequence [TR=196 ms, 3 ms interval between two echoes, slice thickness=2 mm, 30° flip angle]. T2 and T2* relaxation times (R2 and R2*) were calculated by fitting an exponential curve to the signal amplitudes as a function of the echo time (TE) for each segmented scaffold region using the Imalytics Preclinical Software. The exponential curve includes an offset to account for a signal plateau created by noise or a component with slow signal decay. Furthermore, T1- and T2-weighted images were acquired using a T1-weighted turbo-spin-echo (TSE) sequence [TR=9 ms, TE=700 ms, slice thickness=2 mm], and a T2- weighted TSE sequence [TR=1200 ms, TE=100 ms, slice thickness=2 mm]. The size and volume of the hydrogels were assessed based on T1- and T2-weighted TSE images using the Imalytics Preclinical Software. At least it can be seen in FIG. 3 the MR Images of Collagen Scaffolds with/-out HL at 3 T MR. T1-(a) and T2-(b) weighted images. 1 to 5 number tags are referring to HL labeled samples C×L 0.1, C×L 0.2, C×L 0.25, C×L 0.5 and Control C×L scaffold without HL correspondingly.

The invention claimed is:

1. Tetrapyrroles conjugated compounds according to formula (I)

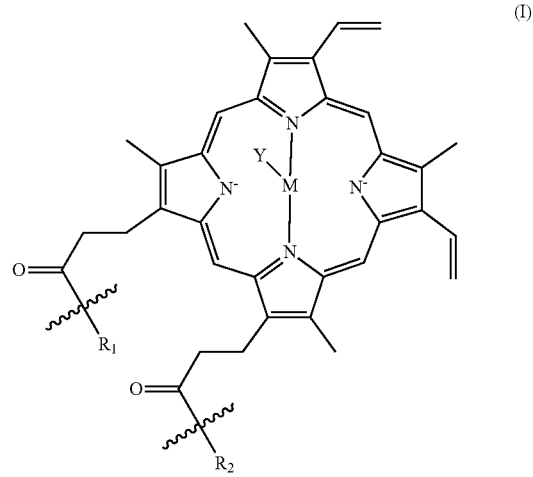

wherein,

M consists of Fe, Ru, Os, Mn, Ni, Co

Y consists F, Cl, Br, I, OH, pyridines, pyrazoles, imidazole, histidine, isothiocyanates, acetonitrile, methanol, wherein a linker with the formula (II)

A = NH-, O, S
B = NH-, O, S
n = 1 to 20 is located between the tetrapyrroles and at least one at least partly water-soluble compound $R_1$ and $R_2$, wherein $R_1$, $R_2$ consists of OH, SH, $NH_2$, HisGLyOMe, polyurethanes, polyacrylates, polystyrenes, polyvinyllactams, PGLA, polyacrylic acid, PVP, hyaluronic acid, arginine, lysine, histidine, PEG, polyether amines, polylysine, polyarginine, polyhistidine and their salts, solvates and solvates of these salts.

2. Tetrapyrroles conjugated compounds according to claim 1, wherein the linker between the tetrapyrroles and the at least partly water-soluble compound is containing ethylenediamine, amino ethanol, ethylene glycol, mercaptoethanol, ethanedithiol.

3. Tetrapyroles conjugated compounds according to claim 2 with the formula (III)

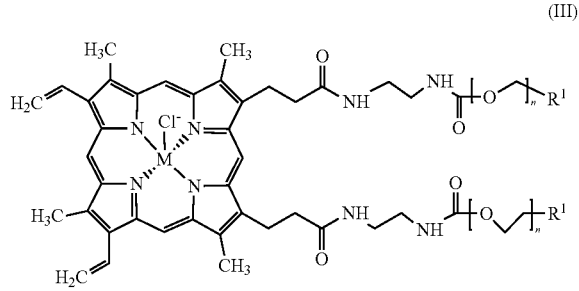

wherein n = 1 to 20 and wherein $R_1$ and $R_2$ are consisting of OH, SH, $NH_2$, HisGlyOMe, polyurethanes, polyacrylates, polystyrenes, polyvinyllactams, PGLA, polyacrylic acid, PVP, hyaloronic acid, arginine, lysine, histidine and PEG, polyether amines, polylysine, polyarginine, polyhistidine and their salts, solvates and solvates of these salts.

4. Tetrapyrroles conjugated compounds according to claim 3 with the formula (IV)
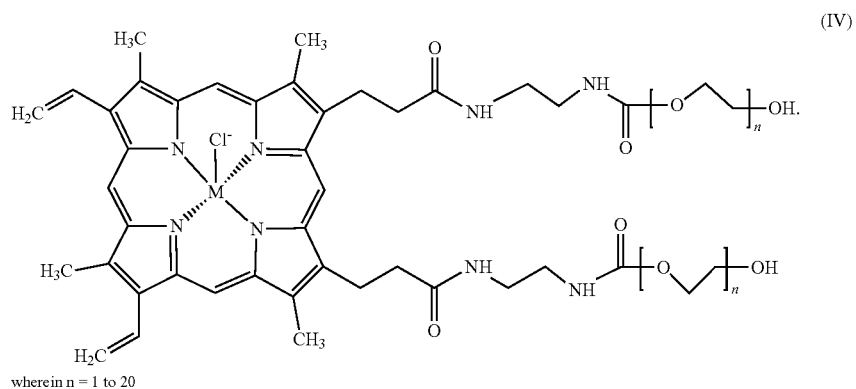
(IV)
wherein n = 1 to 20
5. A method of performing MRI, comprising administering a contrast agent to a subject, wherein the contrast agent comprises one or more a tetrapyrroles conjugated compound according to claim 1.
* * * * *